United States Patent

Neri et al.

[11] Patent Number: 5,852,084
[45] Date of Patent: Dec. 22, 1998

[54] CRYSTALLINE FORM OF TETRAKIS-(2,4-DI-T-BUTYLPHENYL)-4,4'-BIPHENYLENE

[75] Inventors: Carlo Neri, S. Donato Mil.se; Marco Bizzarri, Trezzo sull'Adda; Luciano Pallini, S. Giuliano Miles, all of Italy

[73] Assignee: Great Lakes Chemical Italia S.r.l., Milan, Italy

[21] Appl. No.: 685,491

[22] Filed: Jul. 24, 1996

[30] Foreign Application Priority Data

Sep. 14, 1995 [IT] Italy .................... MI95A1914

[51] Int. Cl.$^6$ ............................ C08K 5/5393; C07F 9/48
[52] U.S. Cl. ............................ 524/126; 558/156
[58] Field of Search ............... 558/156; 524/126

[56] References Cited

U.S. PATENT DOCUMENTS

| | | | |
|---|---|---|---|
| 3,825,629 | 7/1974 | Hofer et al. | 524/119 |
| 4,418,030 | 11/1983 | Muller et al. | 264/142 |
| 4,578,021 | 3/1986 | Schermutzki | 425/6 |
| 4,769,200 | 9/1988 | Hupfer et al. | 264/143 |
| 4,957,956 | 9/1990 | Neri et al. | 524/126 |
| 4,985,481 | 1/1991 | Neri et al. | 524/126 |
| 5,109,043 | 4/1992 | Bohshar et al. | 524/126 |
| 5,298,541 | 3/1994 | Bohshar et al. | 524/126 |
| 5,300,257 | 4/1994 | Akashi et al. | 524/126 |
| 5,334,739 | 8/1994 | Pastor et al. | 524/119 |
| 5,373,040 | 12/1994 | Pastor et al. | 524/119 |

FOREIGN PATENT DOCUMENTS

| | | |
|---|---|---|
| 0 374 761 | 6/1990 | European Pat. Off. . |
| 1 372 528 | 10/1974 | United Kingdom . |
| WO 94 12506 | 3/1978 | WIPO . |
| WO 94 12509 | 6/1994 | WIPO . |

*Primary Examiner*—Veronica P. Hoke
*Attorney, Agent, or Firm*—Oblon, Spivak, McClelland, Maier & Neustadt, P. C.

[57] ABSTRACT

Tetrakis-(2,4-di-t-butylphenyl) -4,4'-biphenylene diphosphonite having the formula:

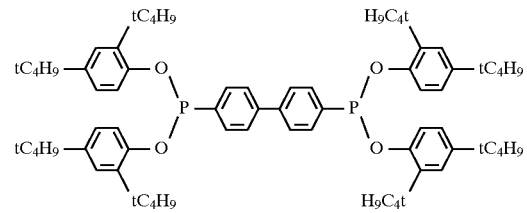

in crystalline form, having a melting point of 185° C.–186° C. The above diphosphonite is useful as a stabilizer in organic polymers.

7 Claims, 3 Drawing Sheets

CRYSTALLINE FORM OF TETRAKIS-(2,4-DI-T-BUTYLPHENYL)-4,4'-BIPHENYLENE

The present invention relates to a new crystalline form of tetrakis-(2,4-di-t-butylphenyl)-4,4'-biphenylene diphosphonite.

More specifically, the present invention relates to a new crystalline form of tetrakis-(2,4-di-t-butylphenyl)-4,4'-biphenylene diphosphonite and its use as a stabilizer in organic polymers.

A further object of the present invention relates to polymeric compositions stabilized with the above diphosphonite.

The tetrakis-(2,4-di-t-butylphenyl)-4,4'-biphenylene diphosphonite described, for example, in English patent 1.372.528 and U.S. Pat. Nos. 3,852,629 and 4,075,163, is a compound having the formula:

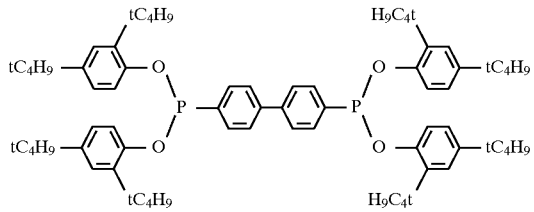

and is used as a stabilizer for organic materials, especially organic polymers which, as is known, are subject to degradation over a period of time due to exposure to atmospheric agents, mainly ultraviolet rays and which also easily undergo degradation during processing and transformation processes owing to the high temperatures reached.

These degradations cause a deterioration in the physical characteristics of organic polymers such as, for example, a decrease in the breaking load and flexibility, which are accompanied by a variation in the viscosity index, as well as alterations in the optical properties of the end-product.

Small quantities of stabilizing compounds are normally introduced into organic polymers to prevent these degradations.

The above patents also describe a process for the preparation of tetrakis-(2,4-di-t-butylphenyl)-4,4' biphenylene diphosphonite which involves the reaction of biphenyl with aluminium trichloride ($AlCl_3$) and phosphorous trichloride ($PCl_3$) to give 4,4'-biphenyl-bis-dichlorophosphine complexed with aluminium trichloride, the separation of the aluminium trichloride from the reaction mass using a suitable complexing agent and the subsequent reaction of 4,4'-biphenyl-bis-dichlorophosphine with 2,4-di-t-butylphenol. Table 1, example 12 of the above patents indicates a tetrakis-(2,4-di-t-butylphenyl)-4,4'-biphenylene diphosphonite, in crystalline form, having a melting point of 94° C.–96° C.

The compound thus obtained is used as such in the stabilization of organic materials alone or combined with other known stabilizers such as, for example, sterically hindered phenols or phosphites.

The commercial product Sandostab P-EPQ®, often indicated as tetrakis-(2,4-di-t-butylphenyl)-4,4'-biphenylene diphosphonite, as is well-known in the art, is not a purely crystalline product but a mixture in which:

tetrakis-(2,4-di-t-butylphenyl)-4,4'-biphenylene diphosphonite approximately represents 70%;

tris-(2,4-di-t-butylphenyl)-phosphite approximately represents 15%;

bis-(2,4-di-t-butylphenyl)-4-biphenyl-phosphonite approximately represents 10%; and 2,4-di-t-butylphenol approximately represents 1.7%.

The Applicant has now surprisingly found a new crystalline form of tetrakis-(2,4-di-t-butylphenyl)-4,4'-biphenylene diphosphonite, having a melting point of 185° C.–186° C., which is white-coloured, with a good flowability and better hydrolytic stability than that of commercially known phosphonites (see FIG. 3 en-closed).

The present invention therefore relates to a tetrakis-(2,4-di-t-butylphenyl)-4,4'-biphenylene diphosphonite having the formula:

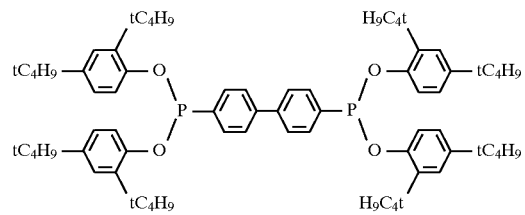

in crystalline form, with a melting point of 185° C.–186° C.

The above tetrakis-(2,4-di-t-butylphenyl)-4,4'-biphenylene diphosphonite was characterized by spectrometry ($^{31}$P-NMR and $^1$H-NMR), DSC ("Differential Scanning Calorimetry") and X-ray diffractometry carried out with a Philips goniometer for powders using CuKα radiation and nickel filter (XRD).

Figure 1:
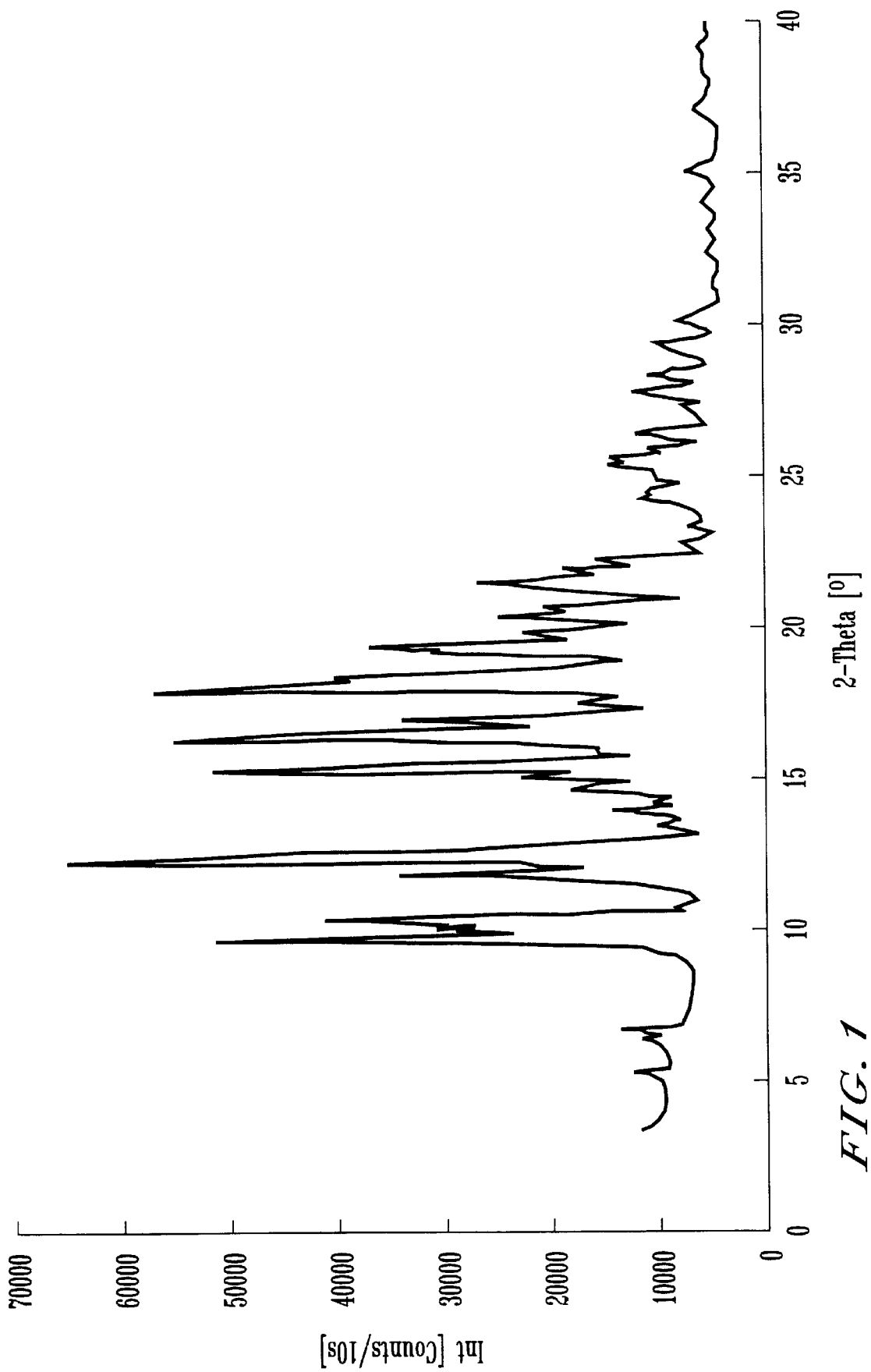
FIG. 1 shows the spectrum relating to the X-ray diffractometric analysis of powders in Example 1.

The results of the spectrometric analyses ($^{31}$P-NMR and $^1$H-NMR) and DSC are shown in the examples, the results of the diffractometric analyses (XRD) are shown in Table 1 and FIG. 1.

The crystalline tetrakis-(2,4-di-t-butylphenyl)-4,4'-biphenylene diphosphonite of the present invention can be prepared with a process which comprises:

(a) reacting biphenyl and phosphorous trichloride ($PCl_3$), in the presence of a Friedel-Crafts catalyst;

(b) separating the biphenyl-bis-dichorophosphines obtained in step (a) by decomposing the adduct with the Friedel-Crafts catalyst using a suitable complexing agent, in the presence of a solvent;

(c) reacting the biphenyl-bis-dichlorophosphines recovered in step (b) with 2,4-di-t-butyl-phenol, in the presence of or without a solvent;

(d) crystallizing the tetrakis- (2,4-di-t-butylphenyl)-4,4'-biphenylene diphosphonite obtained in step (c), in the presence of a solvent.

The preferred Friedel-Crafts catalyst in step (a) of the above process is aluminium trichloride ($AlCl_3$). In this case molar ratios biphenyl/$PCl_3$/$AlCl_3$ are used of between 1/2/2 and 1/10/5, preferably between 1/5/2 and 1/8/4. Step (a) is carried out at a temperature of between 40° C. and 80° C., preferably between 60° C. and 75° C. and for a time of between 5 and 12 hours, preferably between 7 and 10 hours. At the end of the reaction the non-reacted phosphorous trichloride is eliminated by distillation at reduced pressure.

In step (b), the separation of the Friedel-Crafts catalyst from the biphenyl-bis-dichlorophosphines is carried out using a suitable complexing agent such as, for example, phosphorous oxychloride (POCl$_3$), tertiary amines, pyridine, etc. In the case of phosphorous oxychloride, which is the preferred complexing agent, the molar ratio POCl$_3$/AlCl$_3$ is between 1/1 and 3/1, preferably between 1/1 and 2/1. Useful solvents in step (b) are phosphorous trichloride (PCl$_3$), hydrocarbides such as, for example, monochlorobenzene, toluol, etc. The biphenyl-bis-dichlorophosphines are then recovered by separating the solution of these from the solid complex of aluminium trichloride (AlCl$_3$) using the normal techniques of centrifugation or filtration and subsequently removing the solvent by evaporation at reduced pressure.

In step (c) the reaction between the biphenyl-bis-dichlorophosphines and the 2,4-di-t-butylphenol is carried out in mass or in the presence of a solvent selected from hydrocarbides such as, for example, monochlorobenzene, toluol, etc., using an excess of 2,4-di-t-butylphenol of between 2% and 30%, preferably between 5% and 25%, removing the hydrochloric acid which is formed during the reaction by passing an inert gas through the mass or by the use of a tertiary amine or pyridine. The reaction is carried out at a temperature of between 100° C. and 170° C., preferably between 120° C. and 160° C., and for a time of between 6 hours and 15 hours, preferably between 8 hours and 13 hours. At the end of the reaction, the possible salt formed is removed by filtration and the solvent is removed by evaporation at reduced pressure.

Crystallization solvents which can be used in step (d) are ketones such as, for example, methylethylketone, acetone, etc. The crystallization is carried out by first heating the reaction mass to the boiling point of the solvent stirring until the complete dissolution of the solid, and subsequently progressively cooling the solution thus obtained to a temperature of between 0° C. and 20° C., maintaining the whole mixture under bland stirring until crystallization takes place. The crystals thus obtained are separated from the solution by filtration and then dried at reduced pressure.

The crystalline tetrakis-(2,4-di-t-butylphenyl)4,4'-biphenylene diphosphonite obtained in step (d) can be subjected to heating to a temperature above its melting point (185° C.–186° C.) and rapid cooling of the molten product thus obtained. In this case a tetrakis-(2,4-di-t-butylphenyl)-4,4'-biphenylene diphosphonite in amorphous form is obtained.

A further object of the present invention therefore relates to a tetrakis-(2,4-di-t-butylphenyl)-4,4,-biphenylene diphosphonite having the formula:

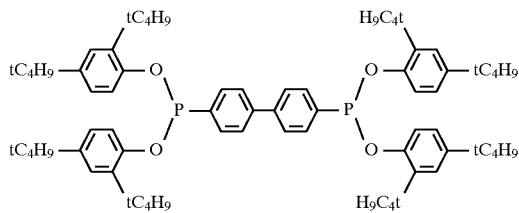

in amorphous form, with a glass transition temperature (T$_g$) within the range of 78° C. to 84° C.

The tetrakis-(2,4-di-t-butylphenyl)-4,4'-biphenylene diphosphonite in amorphous form was characterized by DSC ("Differential Scanning Calorimetry") and X-ray diffractometry carried out with a Philips goniometer for powders using CuKα radiation and a nickel filter (XRD).

Figure 2:
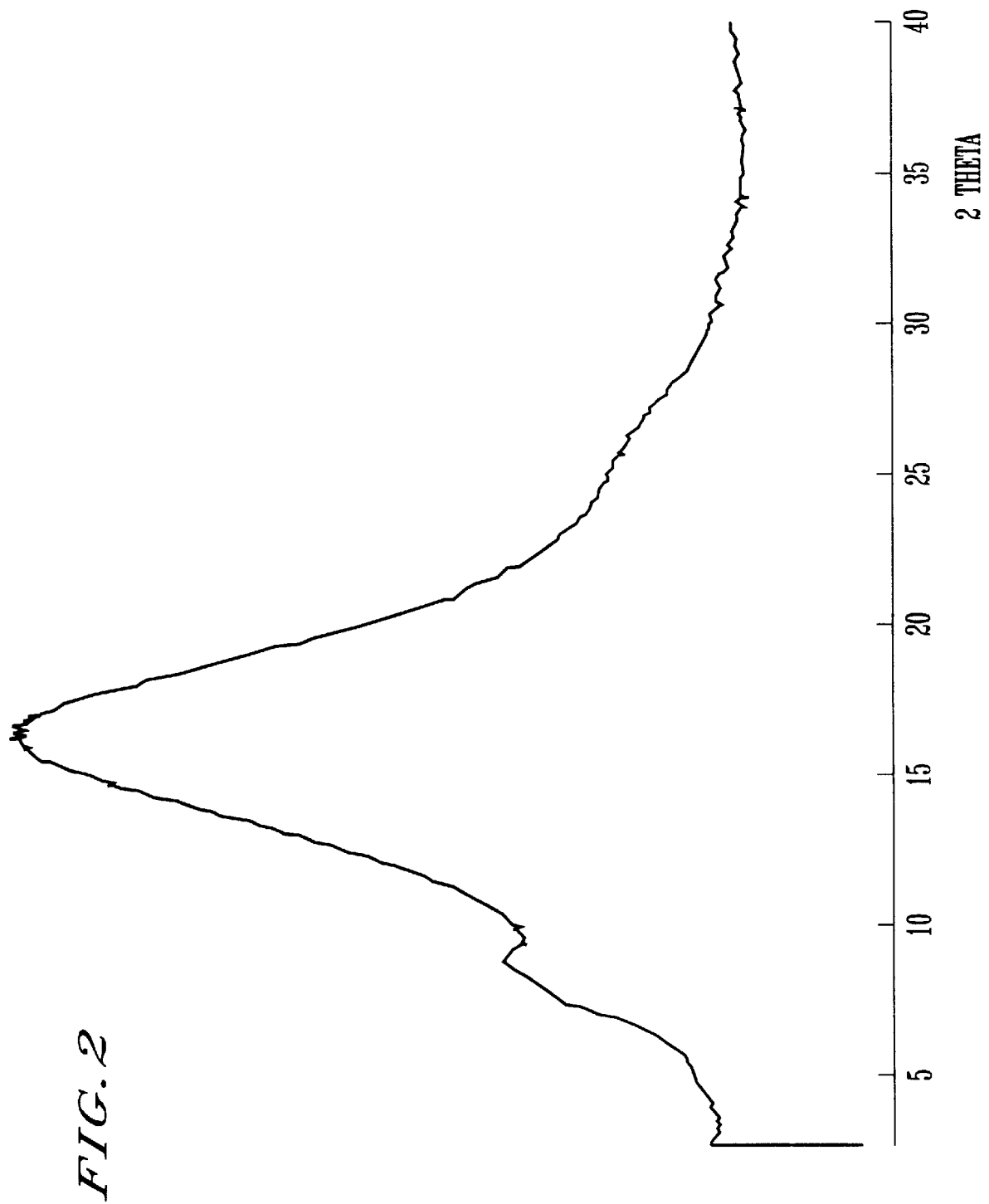
FIG. 2 shows the spectrum relating to the X-ray diffractometric analysis of powders in Example 2.

The results of the DSC analysis are shown in the examples, the results of the diffractometric analysis (XRD) are indicated in FIG. 2.

Figure 3:
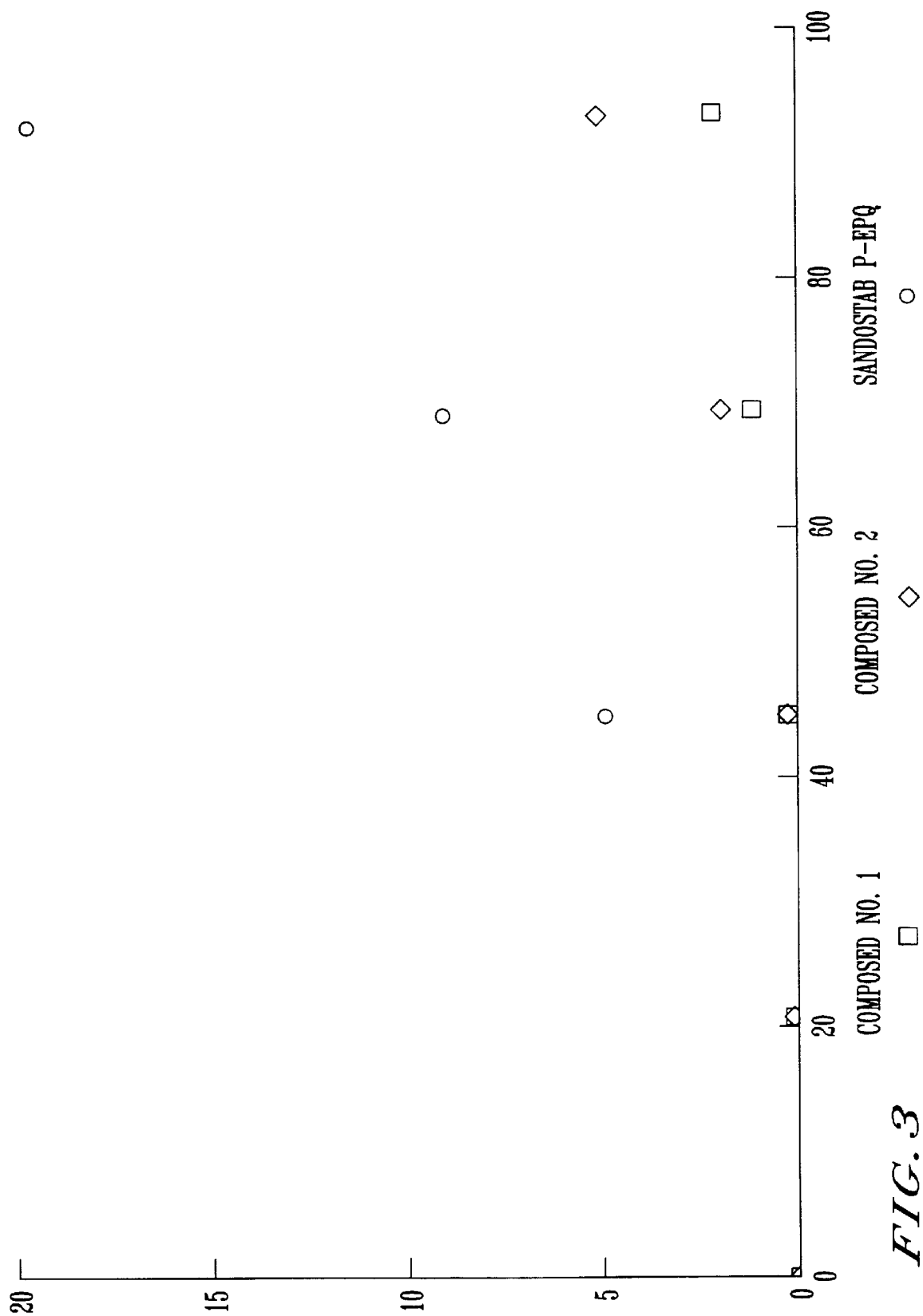
FIG. 3 shows the gas-chromatographic analytic dosagin of 2,4-di-t-butylphenol released during the oven treatment in Example 3.

Tetrakis-(2,4-di-t-butylphenyl)-4,4'-biphenylene diphosphonite in amorphous form has a hydrolytic stability which is greater than that of the known commercial phosphonites (see FIG. 3 enclosed).

The rapid cooling of the molten product, suitable for causing its rapid solidification, can be obtained with any known method in the art.

The preferred methods are:

pouring the molten product onto a cold metal sheet, for example, at a temperature equal to or less than room temperature;

pouring the molten product into a non-solvent, non-reactive and cold liquid, for example, at a temperature equal to or less than room temperature;

cooling the molten product in drops in gas (for example nitrogen) with a technique similar to prilling.

The above techniques allow the production, depending on the circumstances, of an amorphous tetrakis-(2,4-di-t-butylphenyl)-4,4'-biphenylene diphosphonite in the form of a solid body to be subjected to flaking and/or grinding, or in the form of free-flowing granules having the desired size.

The tetrakis-(2,4-di-t-butylphenyl)-4,4'-biphenylene diphosphonite, both in crystalline and amorphous form, (hereafter tetrakis-(2,4-di-t-butylphenyl)-4,4'-biphenylene diphosphonite must be considered as being in both crystalline and amorphous form), of the present invention can be used in the stabilization of any organic polymer against oxidative degradation caused by light and/or heat such as, for example, olefinic polymers, polycarbonates, polyesters, polymeric alloys, ABS, etc.

Consequently another aspect of the present invention relates to stabilized polymeric compositions which comprise an organic polymer and a stabilizing quantity of the tetrakis-(2,4-di-t-butylphenyl)-4,4'-biphenylene diphosphonite of the present invention.

In general, the tetrakis-(2,4-di-t-butylphenyl)-4,4'-biphenylene diphosphonite of the present invention can be incorporated into the polymeric compositions to be stabilized thereby, in a quantity of between 0.005% and 5% by weight.

The quantity of stabilizing compound used may vary, however, depending on the polymeric substrate to be stabilized and the use of the end-product. In the preferred embodiment the polymeric compositions contain a quantity of stabilizer of between 0.005% and 2%, preferably between 0.05% and 1% by weight.

The tetrakis-(2,4-di-t-butylphenyl)-4,4'-biphenylene diphosphonite of the present invention can be incorporated into the organic polymers with the conventional techniques before the production phase of the end-products. For example, the stabilizing powder can be mixed with the polymer powder, or a suspension or emulsion of the stabilizer can be mixed with the polymer powder or with a suspension or emulsion of the polymer.

The stabilized polymeric composition, further object of the present invention, can optionally contain various conventional additives or their mixtures in a quantity of between 0.01% and 5%, preferably between 0.025% and 2%, more preferably between 0.1% and 1% by weight. For example, among the conventional additives, phosphites, sterically hindered amines or other stabilizers to light and ultraviolet rays, sterically hindered phenols, "metal-deactivators", hydroxylamines, basic co-stabilizers, nucleating agents, reinforcing fillers and agents, other additives such as, for example: plasticizers, lubricants, emulsifying agents, pigments, optical glossing agents, flame-retardants, antistatic agents, expansion agents, thiosynergists (for example, dilauryl thiodipropionate or distearyl thiodipropionate), can be mentioned.

Some illustrative examples are given below to provide a better understanding of the present invention and for its embodiment, but they should in no way be conidered as limiting the scope of the invention itself.

EXAMPLE 1

Tetrakis-(2,4-di-t-butylphenyl)-4,4'-biphenylene diphosphonite in crystalline form (Compound N° 1). operating in an inert atmosphere, 40 g of biphenyl, 240 g of phosphorous trichloride and 104.6 g of aluminium trichloride are mixed in a 500 ml flask, equipped with a propeller stirrer, thermometer and condenser.

The mixture is heated to the boiling point of the phosphorous trichloride (75° C.), the reaction mass being maintained under vigorous stirring and the hydrochloric acid which develops being trapped in water. The reaction mass is maintained under these conditions for 7–8 hours.

At the end of the reaction the non-reacted phosphorous trichloride is eliminated by distillation at reduced pressure.

The red oil obtained is suspended in 300 g of monochlorobenzene, cooled to 10° C. and 120.3 g of phosphorous oxychloride are added dropwise to the cold suspension thus obtained, maintained under vigorous stirring. The yellowish-white solid which is formed is separated by filtration.

The filtrate obtained is subjected to distillation of the monochlorobenzene at reduced pressure and 86.2 g of a yellow-orange oil are obtained.

The oil obtained is redissolved in 350 g of monochlorobenzene and 240 g of 2,4-di-t-butylphenol are added to this solution.

The reaction mass is brought to the boiling point of the monochlorobenzene (132° C.) and the hydrochloric acid which is released during the reaction is suitably trapped in water. The reaction mass is maintained in these conditions, under stirring, for 12 hours.

The monochlorobenzene and the non-reacted 2,4-di-t-butylphenol are eliminated by distillation at reduced pressure. 239 g of a yellowish solid are obtained, which are mixed with 480 ml of methylethylketone in a 1 litre flask, equipped with a propeller stirrer, thermometer and condenser.

The mass is heated to 80° C. and stirred until the complete dissolution of the solid. The solution is then gradually cooled to 10° C. and maintained under slow stirring until crystallization takes place.

The crystals obtained are collected by filtration, washed with cold methylethylketone and then dried at reduced pressure.

80 g of crystalline tetrakis-(2,4-di-t-butylphenyl)-4,4'-biphenylene diphosphonite (Compound N° 1) are obtained, having the following characteristics:

Melting point (DSC): 185.7° C.; ΔH=62.4 J/g;

$^{31}$p-NMR (200 MHz, CDCl$_3$—H$_3$PO$_4$) δ (ppm) (decoupled by proton): −154 s (2P);

−$^{31}$p-NMR (200 MHz, CDCl$_3$—H$_3$PO$_4$) δ (ppm) (not decoupled by proton): −154 t (2P);

$^{31}$p-NMR (200 MHz, CDCl$_3$—H$_3$PO$_4$) δ (ppm): 8.03 m (4H), 7.78 m (4H); 7.35 m (4H); 7.14 m (8H); 1.35 s (36H); 1.31 s (36H);

Purity (gas-chromatography) : >98%.

FIG. 1 shows the spectrum relating to the X-ray diffractometric analysis from powders (XRD).

Table 1 indicates the list of the main reflections relating to the X-ray diffractometric analysis from powders (XRD).

TABLE 1

| d (Å)[a] | I/I$_o$ 100[b] | d (Å)[a] | I/I$_o$ 100[b] |
|---|---|---|---|
| 14.6 ± 0.2 | w | — | — |
| 17.8 ± 0.2 | w | 5.10 ± 0.06 | w |
| 13.9 ± 0.2 | w | 4.96 ± 0.05 | m |
| 9.2 ± 0.1 | vs | 4.91 ± 0.05 | vs |
| 8.9 ± 0.1 | s | 4.84 ± 0.05 | s |
| 8.7 ± 0.1 | s–vs | 4.66 ± 0.05 | s |
| 7.58 ± 0.08 | s | 4.61 ± 0.05 | s |
| 7.39 ± 0.08 | m | 4.51 ± 0.05 | m |
| 7.14 ± 0.08 | vs | 4.39 ± 0.04 | m |
| 7.03 ± 0.08 | m | 4.33 ± 0.04 | m |
| 6.71 ± 0.08 | w | 4.17 ± 0.04 | m |
| 6.46 ± 0.08 | w | 4.08 ± 0.04 | w |
| 6.12 ± 0.08 | m | 4.03 ± 0.04 | w |
| 5.96 ± 0.06 | m | 3.95 ± 0.03 | w |
| 5.78 ± 0.06 | vs | 3.85 ± 0.03 | w |
| 5.67 ± 0.06 | m | 3.70 ± 0.03 | w |
| 5.55 ± 0.06 | m | 3.66 ± 0.03 | w |
| 5.49 ± 0.06 | m | 3.60 ± 0.03 | w |
| 5.40 ± 0.06 | vs | 3.54 ± 0.03 | w |
| 5.27 ± 0.06 | s | 3.51 ± 0.03 | w |

[a]= interplane distance;
[b]= relative intensity: vs = very strong (60–100); v = strong (40–60); m = medium (20–40); w = weak (0.20).

EXAMPLE 2

Tetrakis-(2,4-di-t-butylphenyl)-4,4'-biphenylene diphosphonite in amorphous form (Compound N° 2).

Operating in an inert atmosphere, 50 g of tetrakis-(2,2-di-t-butylphenyl)-4,4 '-biphenylene diphosphonite in crystalline form (Compound N° 1) obtained in example 1 are put into a 100 ml, two-neck flask, equipped with a propeller stirrer, thermometer and condenser.

The mass is gradually heated to 195° C. until the crystals have completely melted.

After about 15 minutes of light stirring at this temperature, the molten product is poured onto a cold aluminium sheet and the solid thus obtained is transformed in the form of flakes. 50 g of tetrakis-(2,2-di-t-butylphenyl)-4,4'-biphenylene diphosphonite in amorphous form (Compound N°2) are obtained with the following characteristics:

Glass transition temperature (DSC): 78° C.–84° C.;

Purity (gas-chromatography): >98%.

FIG. 2 shows the spectrum relating to the X-ray diffractometric analysis from powders (XRD).

EXAMPLE 3

The hydrolytic stability of tetrakis-(2,2-di-t-butylphenyl)-4,4'-biphenylene diphosphonite in crystalline form (Compound N° 1) of example 1 and in amorphous form (Compound N° 2) of example 2 is compared with the commercial product known as Sandostab P-EPQ®.

Four aluminium capsules containing about 1 g of each compound are prepared for each compound to be tested (Compound N° 1, Compound N° 2 and Sandostab P-EPQ®).

The capsules are numbered from 1 to 4 and subsequently placed in a closed oven and maintained at a temperature of 55° C. and 100% of relative humidity.

The capsules are then removed from the oven at various times as shown in Table 2 below.

TABLE 2

| CAPSULE N° | TIME (hours) |
|---|---|
| 1 | 21 |
| 2 | 45 |
| 3 | 69 |
| 4 | 93 |

The compound contained in the capsule is dissolved in toluene, filtered to eliminate any possible turbidity present and subjected to gas-chromatographic analytic dosaging of the 2,4-di-t-butylphenol released during the above oven treatment. The results thus obtained are shown in FIG. 3 (in abscissa there is the time in hours and in ordinate the % of gas-chromatographic 2,4-di-t-butylphenol).

EXAMPLE 4

The process stabilizing activity of the compound obtained in example 1 (Compound N° 1) is compared with that of the commercial product Sandostab P-EPQ®.

The activity is measured by evaluating the "Melt Flow Index" (MFI) and the Yellow Index (YI) at the 1st, 3rd and 5th extrusion using polypropylene (MOPLEN FLF 20®) or polyethylene (LLDPE ERACLEAR FP 180®) to which 0.1% by weight of the compound to be tested has been added.

The repeated extrusions were carried out in a Brabender extruder equipped with a clyinder having a diameter of 19 mm and a length of 475 mm, with a compression ratio of 1:4, at a rate of 50 revs per minute.

The temperature profile along the extruder was:

190°-235°-235°-270° C. in the case of polypropylene;

190°-215°-240°-240° C. in the case of polyethylene.

The granules obtained after the 1st, 3rd and 5th extrusion were analyzed determining the MFI value (ASTM D-1238) and the YI value (ASTM D-1925).

The results obtained are shown in Table 3 and Table 4.

TABLE 3

| POLYPROPYLENE | MFI | | | YI | | |
|---|---|---|---|---|---|---|
| | 1st | 3rd | 5th | 1st | 3rd | 5th |
| Polymer as such | 28.0 | 54.5 | 75.9 | −4 | −3.3 | −3.3 |
| Sandostab P-EPQ ® | 13.1 | 14.7 | 16.2 | −3.4 | −2.5 | −1.6 |
| Compound N° 1 | 13.3 | 14.3 | 16.0 | −4.1 | −3.6 | −2.8 |

TABLE 4

| POLYETHYLENE | MFI | | | YI | | |
|---|---|---|---|---|---|---|
| | 1st | 3rd | 5th | 1st | 3rd | 5th |
| Polymer as such | 2.68 | 2.459 | 2.53 | −2.1 | 0.3 | 1.6 |
| Sandostab P-EPQ ® | 2.72 | 2.66 | 2.62 | −3.2 | −0.5 | 0.7 |
| Compound N° 1 | 2.77 | 2.80 | 2.80 | −3.2 | −1.2 | −0.2 |

We claim:

1. Tetrakis-(2,4-di-t-butylphenyl)-4,4'-biphenylene diphosphonite having the formula:

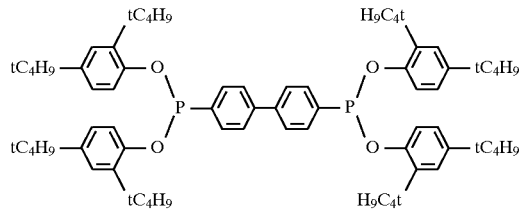

in crystalline form, having a melting point of 185° C.–186° C.

2. Tetrakis-(2,4-di-t-butylphenyl)-4,4'-biphenylene diphosphonite having the formula:

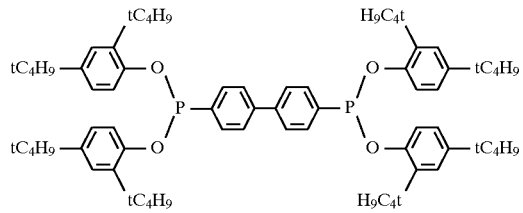

in amorphous form, having a glass transition temperature ($T_g$) within the range of 78° C. and 84° C.

3. Stabilized polymeric compositions which comprise an organic polymer and a stabilizing quantity of tetrakis-(2,4-di-t-butylphenyl)-4,4'-biphenylene diphosphonite in crystalline form according to claim 1.

4. Stabilized polymeric compositions which comprise an organic polymer and a stabilizing quantity of tetrakis-(2,4-di-t-butylphenyl)-4,4'-biphenylene diphosphonite in amorphous form according to claim 2.

5. Polymeric compositions according to claim 3 or 4, wherein the organic polymer is selected from olefinic polymers, polycarbonates, polyesters, polymeric alloys, and acrylonitrile-butadiene-styrenecopolymers.

6. The tetrakis-(2,4-di-t-butylphenyl)-4,4'-biphenylene diphosphonite of claim 1, formed by (a) reacting a biphenyl with phosphorous trihalide in the presence of a catalyst to form a biphenyl-bis-dihalophospine; (b) reacting said biphenyl-bis-diphosphine with 2,4,-di-t-butyl-phenol.

7. The amorphous form of the tetrakis-(2,4-di-t-butylphenyl)-4,4'-biphenylene diphosphonite of claim 2, formed by heating said tetrakis-(2,4-di-t-butylphenyl)-4,4'-biphenylene diphosphonite to a temperature above the melting point of said tetrakis-(2,4-di-t-butylphenyl)-4,4'-biphenylene diphosphonite and cooling a molten product thus formed.

* * * * *

UNITED STATES PATENT AND TRADEMARK OFFICE
CERTIFICATE OF CORRECTION

PATENT NO. : 5,852,084

DATED : December 22, 1998

INVENTOR(S): Carlo NERI, et al.

It is certified that an error appears in the above-identified patent and that said Letters Patent is hereby corrected as shown below:

On the title page, item [54] and on top of column 1, line 3, the last word of the title has been omitted. It should be:

--DIPHOSPHONITE--

On the title page, item [75], the third inventor's residence should be:

--S. Guiliano Mil.se--

Signed and Sealed this

First Day of June, 1999

*Attest:*

Q. TODD DICKINSON

*Attesting Officer*         *Acting Commissioner of Patents and Trademarks*

UNITED STATES PATENT AND TRADEMARK OFFICE
CERTIFICATE OF CORRECTION

PATENT NO. : 5,852,084
DATED : December 22, 1998
INVENTOR(S): Carlo NERI et al.

It is certified that an error appears in the above-identified patent and that said Letters Patent is hereby corrected as shown below:

On the title page, delete item [54] in its entirety and replace with --[54] CRYSTALLINE FORM OF TETRAKIS-(2,4-DI-T-BUTYLPHENYL)-4,4'-BIPHENYLENE DIPHOSPHONITE--.

Column 3, line 46, "tetrakis-(2,4-di-t-butylphenyl)-4,4,-biphenylene" should read --tetrakis-(2,4-di-t-butylphenyl)-4,4'-biphenylene--.

Column 5, line 6, "condidered" should read --considered--.
    Line 63, ": >98%" should read -- : $\geq$98%--.

Column 6, line 47, ": >98%" should read -- : $\geq$98%--.

Column 8, line 50, "acrylonitrile-butadiene-styrenecopolymers" should read --acrylonitrile-butadiene-styrene copolymers--.

Signed and Sealed this

Fifteenth Day of May, 2001

Attest:

NICHOLAS P. GODICI

Attesting Officer    Acting Director of the United States Patent and Trademark Office